United States Patent [19]

Iams et al.

[11] Patent Number: 4,890,606

[45] Date of Patent: Jan. 2, 1990

[54] USER CONTROLLED DEVICE FOR DECOMPRESSING THE SPINE

[75] Inventors: John F. Iams, Poway; Robson L. Splane, Jr., Granada Hills, both of Calif.

[73] Assignee: Superspine, Poway, Calif.

[21] Appl. No.: 40,841

[22] Filed: Apr. 21, 1987

[51] Int. Cl.⁴ .................................................. A61F 5/04

[52] U.S. Cl. .......................................... 128/75; 128/71

[58] Field of Search ................ 129/75, 71, 84 R, 84 C

[56] References Cited

U.S. PATENT DOCUMENTS

| | | | |
|---|---|---|---|
| 951,560 | 3/1910 | Eaton | 128/75 |
| 1,356,365 | 10/1920 | Hosmer | 128/75 |
| 3,205,888 | 9/1965 | Stroop | 128/57 |
| 3,540,724 | 11/1970 | Hunter | 272/63 |
| 3,920,240 | 11/1975 | Ross | 272/57 R |
| 3,947,023 | 3/1976 | Martin | 272/57 R |
| 4,232,863 | 11/1980 | Roach | 272/111 |
| 4,356,816 | 11/1982 | Granberg | 128/71 |
| 4,372,552 | 2/1983 | Carlmark | 128/75 |
| 4,502,682 | 3/1985 | Miller | 128/75 |
| 4,524,763 | 6/1985 | Eberling, Jr. | 128/75 |
| 4,534,341 | 8/1985 | Bart et al. | 128/75 |
| 4,603,689 | 8/1986 | Harne | 128/75 |
| 4,620,701 | 11/1986 | Mojden | 272/63 |
| 4,688,557 | 8/1987 | Bradstreet | 128/75 |

FOREIGN PATENT DOCUMENTS

| | | | |
|---|---|---|---|
| 1243327 | 6/1967 | Fed. Rep. of Germany | 128/75 |
| 2410839 | 9/1975 | Fed. Rep. of Germany | 128/75 |
| 3104832 | 1/1983 | Fed. Rep. of Germany | 128/75 |
| 3401238 | 7/1985 | Fed. Rep. of Germany | 128/75 |
| 2332005 | 6/1977 | France | 128/75 |

*Primary Examiner*—Edgar S. Burr
*Assistant Examiner*—Tonya Lamb
*Attorney, Agent, or Firm*—Dressler, Goldsmith

[57] ABSTRACT

An apparatus is described for decompressing the spine from a seated position. Two triangular sides having forearm supports which can be set at an angle to the horizontal plane with the angle having a range of 20°–45° and is attached through cross members and have hand grips mounted adjacent the forearm supports. The apparatus rests on a floor, the ground, a chair or similar subsurface. The user positions himself in a seated position between the sides and raises his body by pressing downward with his forearms and hands, thus unloading and decompressing the spine and lumbar back. An optional harness suspended from above the person may be used to maintain continuous decompression of the lower spine between the upward movements executed by the user, or lower body restraints may be used to permit decompression of only the upper spine. An optional back flexion bar may be used to provide additional directions of movement to the spine.

22 Claims, 3 Drawing Sheets

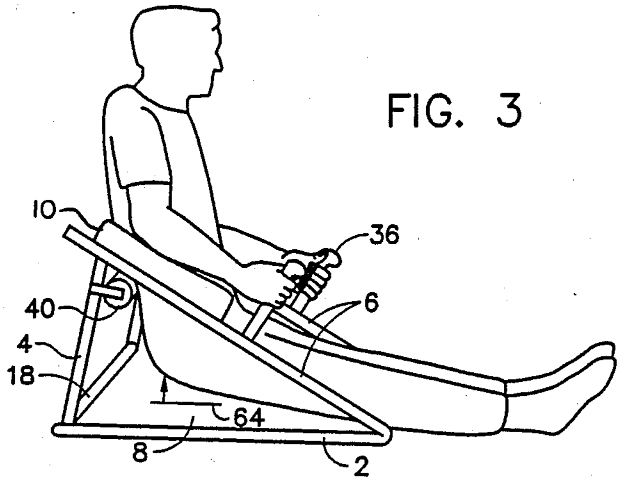
FIG. 3
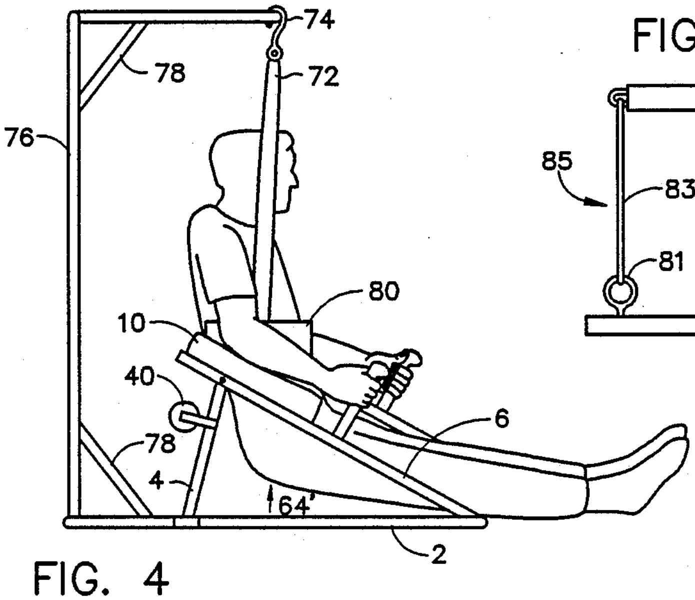
FIG. 4
FIG. 8
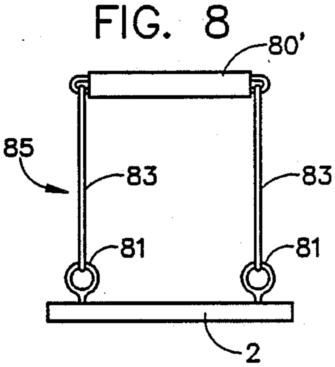
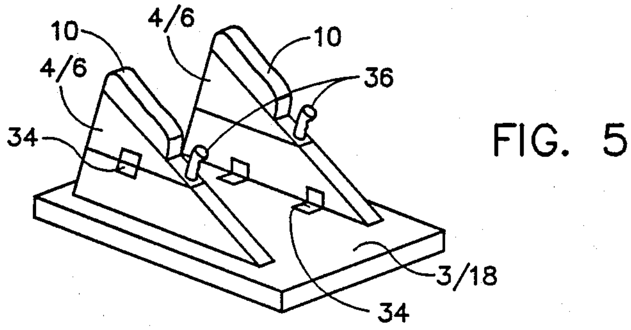
FIG. 5

USER CONTROLLED DEVICE FOR DECOMPRESSING THE SPINE

FIELD OF THE INVENTION

The invention herein relates to exercise and physical therapy equipment. More particularly it relates to such equipment for providing exercise and therapy to a person's spine and lumbar back region.

BACKGROUND OF THE INVENTION

Many people suffer from spinal and lumbar back problems which should be responsive to exercise or physical therapy. Devices have been developed which are claimed to be of value in dealing with such problems, but such devices have suffered from a number of shortcomings.

1. These devices are frequently large and bulky and can be used conveniently only in a clinical or exercise center environment. They are not readily portable and do not lend themselves to use in a home or outpatient setting.

2. Such devices do not provide for unloading of the spine other than by active traction. Such active traction devices are difficult for a patient to use; frequently the assistance of one other person is required to enable a patient to be properly placed in and use the traction device.

3. Most importantly, such devices normally dictate the force to be applied to the patient, rather than allowing the patient to control the force. While such devices usually permit different force settings (often in incremental steps, as by changing the number of weights attached to the traction device), once the particular load is set the patient cannot vary that load and the resultant force during the exercise or therapy session. This presents a serious problem for many patients, in that exercise under a constant force causes severe pain. Typically such a patient suffers immobility in the spine and lumbar back region and must begin any exercise or therapy session slowly and under very little load. As the session continues and the patient's spine and lumbar back begin to loosen, the patient should be able to increase the load and force without reaching an uncomfortable pain level. If pain increases during the session the patient should be able to reduce the load and force to control the pain level. These changes may of course be repeated many times during an exercise or therapy session.

At the present time no exercise or therapy devices permit a patient to be "in the loop" with respect to such control and regulation of spine and lumbar back exercise and therapy. At best the user can only stop the device and manually reset the load or direct a therapist or attendant to do so. Frequent or repeated changes are difficult and inconvenient to accomplish.

4. Such devices often put excessive stress on one or more other parts of the body while attempting to provide relief to the spine and lower back. A common and very simple exercise is where the person stands between two horizontal hand supports placed at about waist height (such as parallel bars or the backs of chairs) and then pushes up on the supports until his arms are straight and his body is lifted off the ground. While this allows the spine to become unloaded, it puts excessive stress on the user's hands and wrists and the position cannot be maintained for more than a few seconds, nor can it be performed for more than a few repetitions before the person's hands and wrists become unduly fatigued.

It would be of considerable value to have an exercise device which is a simple structure allowing for unloading of the user's spine and lumbar back region for prolonged periods, which is readily portable and usable in a variety of settings including the home environment, which does not require the presence of attendants to assist the user and which, most importantly, is under the immediate and continuous control of the user.

BRIEF DESCRIPTION OF THE INVENTION

The invention herein is an apparatus for decompressing the spine of a user positioned in a generally seated posture, which comprises:

a. a frame disposed to rest on an underlying generally rigid subsurface, and having two parallel spaced apart sides, each side having an elevation leg and a support leg supported by the subsurface, and a spacer leg, the legs forming a generally triangular side, and the sides being interconnected by cross members;

b. arm rest means with each support leg to provide support to a user's forearm and grip means projecting upwardly from the support leg adjacent the arm rest means to provide a gripping surface for a user's hand; and c. each support leg being elevated at an angle of about 20° to about 45° above the horizontal, with the angle being maintained by the respective elevation leg; whereby a user can by pushing with his forearms and hands against said arm rest means elevate himself with respect to the subsurface and thereby decompress his spine.

In preferred embodiments the device is adjustable within the defined angular range, has attached means for performing simultaneous leg exercises, has means for providing flexural motion to the spine or has an attached harness which permits the user to move back and forth from active to passive traction repeatedly and at will while using the device. The device can also be made to collapse into a compact structure for easy portability. Another embodiment is adapted to be secured to a chair, such as a secretarial chair, so that it can be used while the person is seated in the chair. Lower body restraint means can also be incorporated into the device to provide decompression of the spine during upward movement by the user.

BRIEF DESCRIPTION OF THE DRAWINGS

FIG. 3 is a perspective view illustrating a typical manner of use of the device.

FIG. 4 is an elevation view illustrating the use of the device in conjunction with an auxiliary harness.

FIG. 5 is a perspective view of another embodiment of the device.

FIG. 8 is a rear elevation view of another lower body securing attachment for the device.

DETAILED DESCRIPTION AND PREFERRED EMBODIMENTS

Figure 1:
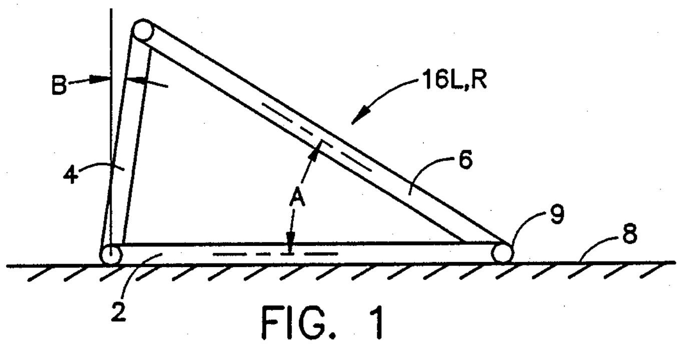
FIG. 1 is a schematic elevation diagram showing the important angular configurations of the device.

The invention and its use is most readily understood by reference to the drawings. FIG. 1 shows schematically an assemblage of the base or spacer leg 2, elevation leg 4 and support leg 6 into a triangular structure defining side 16. In this embodiment the support leg 6 and base leg 2 meet at 9 to form angle A. It will be evident from FIG. 7, however, that the two components do not actually need to be joined as long as their projection also forms angle A. There is an underlying support 8 which is typically a floor, the ground, a table or a similar rigid substrate. While a more resilient supporting substrate, such as a bed, could be used, that would be possible only where the user's buttocks and upper legs can be lifted enough to decompress the spine. In the embodiment shown in FIG. 9 the support is the chair seat frame 102.

Figure 7:
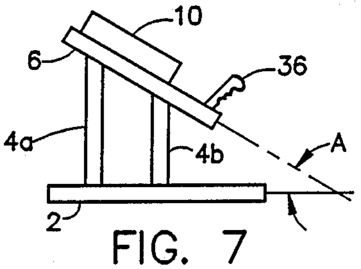
FIG. 7 is a side view of another embodiment of the device.

The triangular structure defines angles A and B. Elevation angle A is the included angle between the support leg 6 and the horizontal plane. In most cases the base leg 2 will be resting on a horizontal substrate 8, as shown in FIG. 1, so that angle A will also be the included angle between the support leg 6 and the base leg 2 and the support leg 6 (or the projections thereof, as shown in FIG. 7). In some cases, the substrate support 8 is not itself horizontal, as with the chair seat frame 102 in FIG. 9 so that the angle between the support leg 6 and the base leg 2 will be different from angle A. It has been found that for proper use of the device, angle A should be in the range of 20° to 45°, preferably 25° to 40° and most preferably about 33° to 35°. If the support legs are elevated to angles outside this range, the user will not have the proper distribution of his or her weight through the forearms and hands; lesser angles place to much weight on the elbows and upper arms, while greater angles place to much weight on the wrists and hands.

Angle B is the angle formed between the elevation leg and a perpendicular to the point at which the elevation leg 4 meets the support 8. This angle is is not critical and can be varied within a fairly wide range. It is preferred that the elevation leg 4 be positioned such that its upper end connects to the support leg 6 at a point generally opposite the user's elbow as illustrated in FIG. 4, to provide the maximum support for the user's body weight and minimize flexing of the support leg 6.

Figure 2:
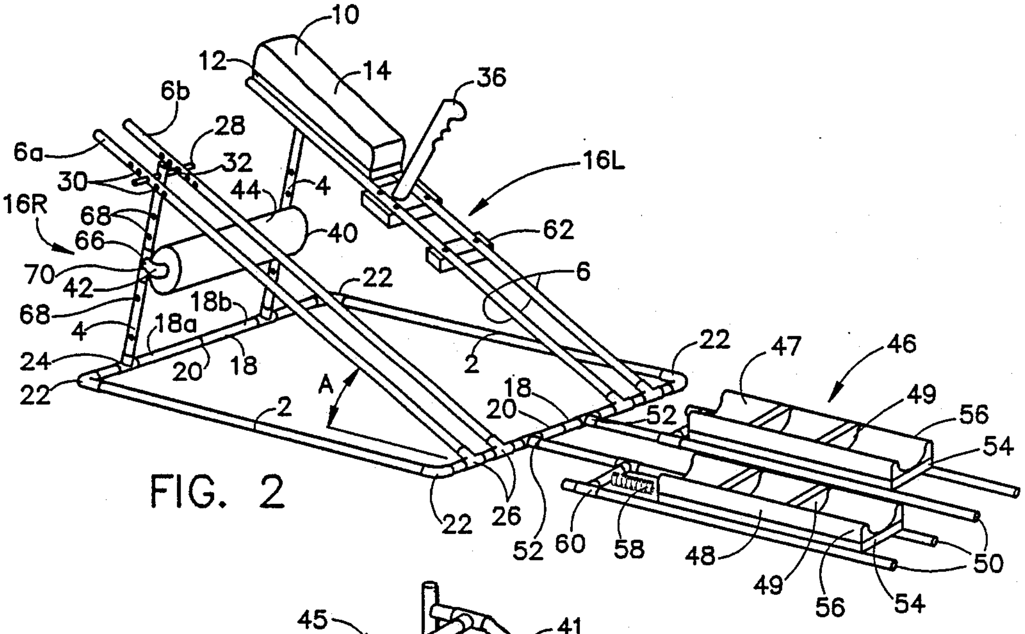
FIG. 2 is a perspective view illustrating one embodiment of the device.

A preferred embodiment of the device is illustrated in FIG. 2. In this particular embodiment the support leg 6 is actually two parallel rods designated 6*a* and 6*b*. It could also be a single flat bar or similar structure capable of supporting arm rests 10 which are formed by base 12 and cushion 14.

There are two parallel units formed by base leg 2, elevation leg 4 and support leg 6 which are designated respectively sides 16L and 16R. These are spaced apart at a width where the user can comfortably place his arms on the arm rests 10. The two sides 16 are maintained at the desired distance by cross members 18. The cross members 18 can be of a fixed length so that the overall apparatus maintains a single width or they can include means to allow for a variable width. This could for instance be accomplished by having one half (18*a*) of each cross member 18 telescope into the other half (18*b*) as shown at 20.

In the embodiment shown in FIG. 2 the device is made of tubular plastic or metal rods. Base legs 2 are joined to cross members 18 by 90° corner members 22. It will be evident of course that the device could be made of any other convenient structural material, such as wood, or any of the various materials could be combined in the structure. Similarly, each of the components can be made in any convenient shape such as elongated rods of circular, polygonal, square or rectangular cross section, angle bars of I, H, T or L cross section or flat boards. For instance, instead of the separate cross members 18 and base legs 2 as shown in FIG. 2, both components could be incorporated into a separate one piece flat base 2/18 from which the elevation legs 4 and support legs 6 extend upwardly, as shown in FIG. 5. Similarly, two upwardly extending triangular shaped flat members 4/6 could encompass an elevation leg 4 and a support leg 6 and be secured on the third side to the base 2/18, as shown in FIG. 5.

In the embodiment shown in FIG. 2 the ends of elevation leg 4 and support leg 6 are joined to tees 24 and 26 respectively which are pivotally mounted for rotation around cross members 18. When the connection between elevation leg 4 and support leg 6 is disconnected as by removal of pin 28 from holes 30 and 32 the apparatus can be folded to a generally flat position and can be easily carried, stored, packaged or shipped. Similar foldability can be achieved with the embodiment of FIG. 5 by the proper placement of hinges 34.

Also mounted on support legs 6 are hand grip handles 36. (It will be noted in FIG. 2 that only a single one of the pair of arm rests 10 and handles 36 is shown, so that the underlying structure of the opposite side 16R can be illustrated. It will be evident that the sides 16R and 16L are identical and that a corresponding arm rest and handle are mounted on the side 16R as shown in FIG. 3.)

With elevation leg 4 and support leg 6 being rotatable around cross members 18 as described above, their relationship to each other can also be changed so that the angle A can be varied as described. One preferred manner of doing this is by having holes 30 drilled in support leg 6, a corresponding hole 32 drilled adjacent the end of elevation leg 4 and a pin 28 which can be inserted through the holes 30 and 32 to align hole 32 with any elected hole 30. Other alternative means of adjusting the angle A by means of elevation leg 4 and support leg 6 will readily suggest themselves to those skilled in the art.

Attached to the support legs 4 is back flexion member 40. This consists of a rigid support 42 extending between elevation members 4, around which is padding 44. This allows the user to conduct back flexion exercises either alone or in conjunction with the other exercises and therapy of this unit, as will be described below. The height of the back flexion bar 40 may be adjusted by sliding the support 42 along elevation leg 4 and aligning the hole 66 with any of the holes 68 and securing the unit by inserting pin 70 in the aligned holes. The back flexion bar 40 may be disposed inwardly of the elevation legs 4 as shown in FIGS. 2 and 3 or may be disposed outwardly of the elevation legs 4 as shown in FIG. 4, depending on the particular type of exercise or therapy to be conducted with the device.

The apparatus may also optionally include leg exercisers 46. These are composed of blocks 48 which slide on supports or rails 50 which in turn are connected to cross member 18, preferably removably through hooks 52. The blocks 48 may be single pieces or may be composed of slides 54 and padding 56. Preferably they are padded as shown in FIG. 2 and the padding 56 is in the form of hollow longitudinal troughs 47 which have foot rests 49 spaced along their length. The blocks 48 are resistive to longitudinal motion so as to provide leg exercise; this may be accomplished by use of tension springs 58 which are secured to cross pieces 60 between rails 50 or by similar use of bungee cords, pistons, etc.

Where desired, to keep parallel components such as support leg components 6*a* and 6*b* in alignment one can use an alignment block such as shown at 62.

Figure 12:
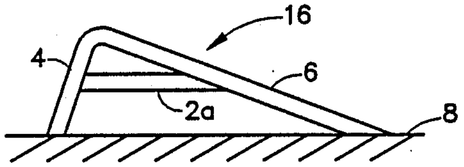
FIG. 12 is a side elevation view of yet another embodiment of the device.

Two other versions of the device are shown in FIGS. 7 and 12. The embodiment shown in FIG. 7 uses two elevations legs 4*a* and 4*b* to support the support leg 6 adjacent opposite ends thereof. This allows the device to be shortened by eliminating the extensions of support leg 6 and base leg 2 to their point of intersection. This more compact embodiment is particularly convenient for storage and transporting.

The device shown in FIG. 12 has sides 16 which are made of one-piece rigid members 4, 6 which are formed into a generally L-shaped configuration. These members 4, 6, incorporating both the elevation leg 4 and the support leg 6, would usually be made of heavy material, such as tubular or angle bar steel or aluminum. The ends of the members 4, 6 rest on the substrate 8 directly without the need for base leg 2. However, stiffener 2*a* is attached to both parts 4 and 6 of member 4, 6 to create a triangular side as with the other embodiments. This is necessary both to prevent the parts 4 and 6 from gradually spreading apart or separating from repeated use and for safety purposes, to prevent the L-shaped member 4, 6 from collapsing (spreading apart) suddenly and causing the user to fall heavily and perhaps sustain injury.

The use of the device is illustrated in FIG. 3. A user sits on the floor 8, or its equivalent as disclosed herein positioned between the support legs 6. The user normally sits with the small of his back positioned against back flexion unit 40, although he may position the unit 40 at some other point on his back or dispense with its presence altogether. The user's forearms rest on supports 10 and his hands grip the hand grips 36. By pressing downward with the hands and forearms, the user raises his body so that his weight is at least in part carried on the forearms and hands and the spine is at least partially decompressed and his weight is at least partially taken off his ischial tuberosities. It is not necessary that the buttocks and upper legs be fully clear of the substrate 8 as indicated at 64, although many users can raise their bodies sufficiently to achieve such clearance, so that all of their weight is carried on their forearms and hands, the spine is fully decompressed and no weight is on the ischial tuberosities.

The user maintains this position as long as possible or as long as directed, then allows himself to settle back on his buttocks with his arms and hands still in the same position. This exercise or therapy is repeated as often as desired or directed. The effect of this exercise is to transfer the user's weight through his shoulder girdle to his forearms and hands and to allow the spine to be unloaded or decompressed by the pull of gravity on his body. Because support for the user's weight is spread throughout the length of his forearms and hands, the hands and wrists do not become rapidly fatigued as with prior art devices. The person can thus maintain himself with a decompressed spine for prolonged periods and can continue repeating the exercise for a significant number of times.

The exercise also has the beneficial effect of inhibiting some muscles in the upper back and shoulders.

Equally important is the person's control over the exercise. He can exert as much or as little force to lift himself as he finds comfortable and can maintain the position for as long or short a time as he wishes, or as may be directed by his therapist or physician. Each repetition of the exercise can be done under different conditions to reflect the loosening and increased mobility of the user's body as the exercise progresses. One can also reduce the time and effort as the he becomes fatigued or begins to sense pain. At no time is the user required to exercise beyond his capabilities or while experiencing pain as would be required by the prior art devices which operate with fixed loads and cycles.

While the person raises his body, he can also flex his spine by leaning backward over the flexion bar 40. This allows him to place two types (or directions) of motion on his spine: axial unloading or decompression motion along the spine and a flexion and extension motion by arching from the sitting position to the back bend position and return. In some instances it is also possible to add a third directional component of motion (rotation) by swiveling the body laterally while bending and/or raising the body.

Another embodiment of the invention is shown in FIG. 4. This embodiment includes a harness 72 suspended as by hook 74 from a gallows frame 76 which may be attached at its lower end to cross members 18 and/or base legs 2 or may be free standing. The gallows frame 76 is stiffened by members 78 against the weight of the user's body. A belt or strap 80 is secured about the user's torso or midsection and supports the user's body raised slightly off the ground as shown at 64'. The portion of the user's spine and back which is below the strap or belt 80 is thus maintained in continuous decompression and the person can put the remainder of his spine into decompression by pushing up from the device as described above. Thus the user can go back and forth between full decompression and partial decompression with the lower spine remaining continually decompressed. This embodiment of the invention is particularly advantageous for infirm patients who have difficulty remaining in an upright seated position without assistance.

Figure 6:
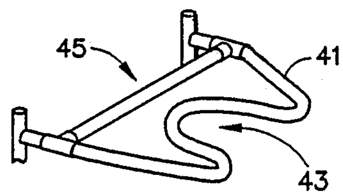
FIG. 6 is a perspective view of a lower body securing attachment for the device.

Other auxillary mechanisms to enhance the exercise or therapy value of this device are shown in FIGS. 6 and 8. The lower body securing unit 45 of FIG. 6 is used in place of bar flexion bar 40 but similarly attached to support legs 4 (not shown) by rigid support 42. Its principal component is W-shaped bar 41. The user sits within the C-shaped central portion 43 of unit 45 so that the bar 41 engages the top of his hips and prevents his lower body from rising when he pushes up with his arms and shoulders. This permits the upper portion of the spine to be decompressed by maintaining the lower body and spine in a fixed position. The same effect is accomplished by the belt unit 85 shown in FIG. 8. This unit 85 consists of a belt 80' which goes about the user's waist and is secured to the base legs 2 or cross members (not shown) through straps 83 connected to deadeyes 81. Alternatively one can restrain the user's upper legs by using leg straps (not shown) secured in a manner similar to straps 83 so that the user cannot elevate his buttocks or legs but still can decompress his spine by pushing upward against such restraint.

Figure 10:
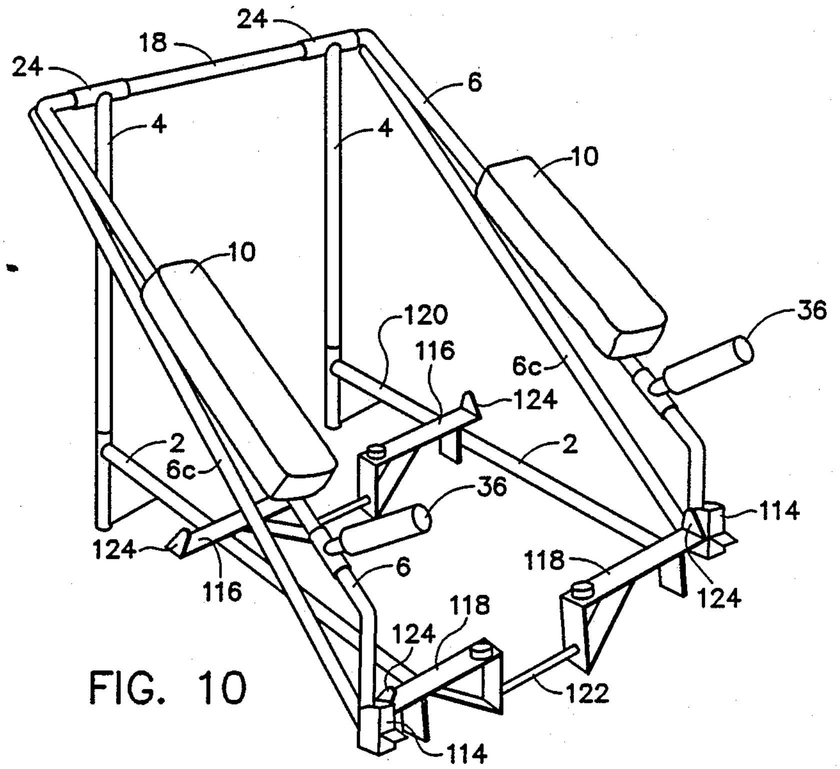
FIG. 10 is a perspective view of the embodiment of FIG. 9.
Figure 9:
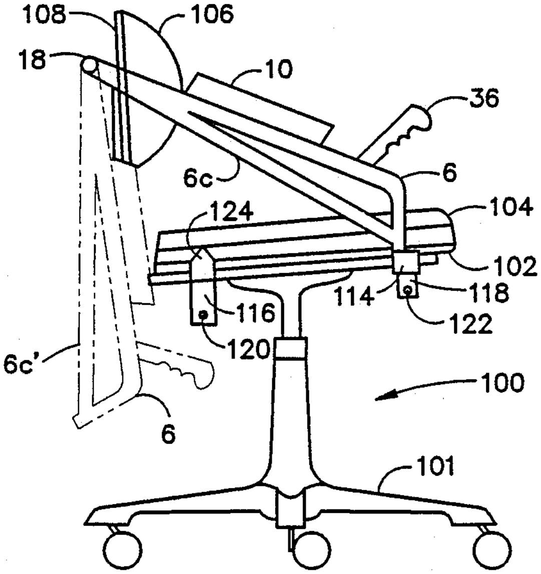
FIG. 9 is a side elevation view of an embodiment of the device mounted on a chair.
Figure 11:
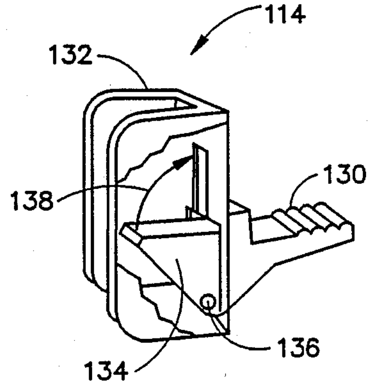
FIG. 11 is a perspective vie of a latching mechanism to secure the embodiment of FIG. 10 to the chair as shown in FIG. 9.

Yet another embodiment is shown in FIGS. 9, 10 and 11. This version of the device is particularly adapted for use in connection with a chair 100 such as a secretary's chair, which has as a seat the chair frame 102 supported by a base 101, a seat cushion 104, and a back rest 106 supported by the upright portion 108 of frame 102. This unit can be adapted for use with many kinds of chairs and is therefore useful for many people whose daily activities require them to sit for long periods. The device is fundamentally similar to the other embodiments, but the base legs 2 and cross members 18 are adapted to connect to the frame 102 of the chair 100 in a semi-permanent fashion. In this embodiment attachment members 116 and 118 are disposed under the frame 102 and connect thereto with hooks 124. Width adjustment and securement is provided by screws 120 and 122 which tighten members 116 and 118 respectively. In the version shown in FIG. 10 the support legs 6 are stiffened by members 6c. The support legs 6 and stiffening members 6c are hinged to cross member 18 through tees 24 and can be lowered to be out of the person's way while working (as indicated in phantom in FIG. 9 at 6' and 6c') and then raised into the use position (with the correct angle A) when the person wishes to exercise. The support legs 6 are secured in the use position by latches 114 shown in FIG. 11. These latches are easily releasable so that the support legs 6 of the device may be quickly moved out of the person's way for work. The latch 114 consists of frame 132 which has catch lever 130 pivoted therein on pin 136. When the latch is locked in place portion 134 of lever 130 engages a mating lug on member 118. When the user wishes to lower the device out of the way, he presses downward on lever 130 which causes portion 134 to pivot upward as indicated by arrow 138 to release from the engagement with the mating lug. With such a device a person who would otherwise be sedentary and confined to a chair for most of his work day with his spine in a compressed state for prolonged periods can readily perform decompression exercises at desired intervals throughout the day and thus improve the condition of his spine and spinal muscles.

It will be evident that there are numerous other embodiments which are not described above but which are clearly within the scope and spirit of the invention. The above description is therefore intended to be exemplary only and the scope of the invention is to be limited solely by the appended claims.

We claim:

1. An apparatus for decompressing the spine of a user positioned in a generally seated posture, which comprises:
   - a. a frame disposed to rest on an underlying generally rigid subsurface, and having two parallel spaced apart sides, each side having an elevation leg and a support leg supported by said subsurface, and a base leg, said legs forming a generally triangular side, and said sides being interconnected by cross members;
   - b. arm rest means with each support leg to provide support to a user's forearm, each arm rest means comprising:
     - b.1 grip means, projecting upwardly from said support leg, to provide a gripping surface for a user's hand, and
     - b.2 cushion rest means, lying along said support leg above the grip means, to provide a surface supporting the elbows and forearms, wherein the elbows, forearms, wrists and hands wedge into the structure of the grip means and cushion means; and
   - c. each support leg being elevated at an angle of about 20° to about 45° above the horizontal, with the angle being maintained by said respective elevation leg;

wherein a user can by pushing with his forearms and hands against said arm rest means elevate himself with respect to said subsurface and thereby at least partially decompress his spine; and wherein the user's forearms and hands wedge into the arm rest means so that the user's upper body weight as transferred through his shoulder girdle is at least partially spread throughout the length of his forearms, reducing fatigue of the hands and wrists.

2. Apparatus as in claim 1 wherein said support legs and said elevation legs are mounted on said cross members adjacent the respective base legs.

3. Apparatus as in claim 2 wherein said support legs and said elevation legs are pivotally mounted to said cross members such that said elevation angle can be varied within said range.

4. Apparatus as in claim 1 wherein said support legs and said elevation legs are attached directly to the respective base legs.

5. Apparatus as in claim 4 wherein said support legs and said elevation legs are pivotally attached to said base legs such that said elevation angle can be varied within said range.

6. Apparatus as in claim 1 further comprising body support means from which said user can be suspended while using said apparatus.

7. Apparatus as in claim 1 wherein said angle is in the range of 25° to 40°.

8. Apparatus as in claim 7 wherein said angle is in the range of 33° to 35°.

9. Apparatus as in claim 1 adapted to be connected to the frame of a chair.

10. Apparatus as in claim 9 further comprising releasable means to allow said support legs to be raised and locked into the desired angle for use while the user is seated in said chair and then to be unlocked and lowered to a position which does not interfere with the user's normal use of the chair.

11. An apparatus for decompressing the spine of a user positioned in a generally seated posture, which comprises:
   - a. a frame disposed to rest on an underlying generally rigid subsurface, and having two parallel spaced apart sides, each side having an elevation leg and a support leg supported by said subsurface, and a base leg, said legs forming a generally triangular side, and said sides being interconnected by cross members;
   - b. arm rest means with each support leg to provide support to a user's forearm and grip means projecting upwardly from said support leg adjacent said arm rest means to provide a gripping surface for the user's hand.

c. each support leg being elevated at an angle of about 20° to about 45° above the horizontal, with the angle being maintained by said respective elevation leg; and d. elongated back flexion means attached at the ends thereof to said elevation legs and disposed intermediate to said base legs and said support legs; whereby a user can by pushing with his forearms and hands against said arm rest means to elevate himself with respect to said subsurface and thereby at least partially decompress his spine.

12. Apparatus as in claim 11 wherein attachment of said back flexion means may be varied along the length of said elevation legs.

13. An apparatus for decompressing the spine of a user positioned in a generally seated posture, which comprises:

a. a frame disposed to rest on an underlying generally rigid subsurface, and having two parallel spaced apart sides, each side having an elevation leg and a support leg supported by said subsurface, and a base leg, said legs forming a generally triangular side, and said sides being interconnected by cross members;

b. arm rest means with each support leg to provide support to a user's forearm and grip means projecting upwardly from said support leg adjacent said arm rest means to provide a gripping surface for a user's hand;

c. each support leg being elevated at an angle of about 20° to about 45° above the horizontal, with the angle being maintained by said respective elevation leg; and d. leg exercise means extending outwardly from the cross member joining said base members at an end of each adjacent said elevation angle, said leg exercise means comprising elongated resistance means providing resistance to a user's leg extension; whereby a user can by pushing with his forearms and hands against said arm rest means elevate himself with respect to said subsurface and thereby at least partially decompress his spine.

14. An apparatus for decompressing the spine of a user positioned in a generally seated posture, which comprises:

a. a frame disposed to rest on an underlying generally rigid subsurface, and having two parallel spaced apart sides, each side having an elevation leg and a support leg supported by said subsurface, and a base leg, said legs forming a generally triangular side, and said sides being interconnected by cross members;

b. arm rest means with each support leg to provide support to a user's forearm and grip means projecting upwardly from said support leg adjacent said arm rest means to provide a gripping surface for a user's hand;

c. each support leg being elevated at an angle of about 20° to about 45° above the horizontal, with the angle being maintained by said respective elevation leg; and d. body support means from which said user can be suspended while using said apparatus, said body support means comprising a gallows frame extending above the user while said user is in said apparatus, and depending downwardly from said gallows frame a harness adapted to encircle and support said user's body in a position elevated above said subsurface but being positioned with respect to said apparatus wherein said user by pushing up on said apparatus with his arms can take the weight of his body off said support means; whereby a user can by pushing with his forearms and hands against said arm rest means elevate himself with respect to said subsurface and thereby at least partially decompress his spine.

15. An apparatus for decompressing the spine of a user positioned in a generally seated posture, which comprises:

a. a frame disposed to rest on an underlying generally rigid subsurface, and having two parallel spaced apart sides, each side having an elevation leg and a support leg supported by said subsurface, and a base leg, said legs forming a generally triangular side, and said sides being interconnected by cross members;

b. arm rest means with each support leg to provide support to a user's forearm and grip means projecting upwardly from said support leg adjacent said arm rest means to provide a hand gripping surface;

c. each support leg being elevated at an angle of about 20° to about 45° above the horizontal, with the angle being maintained by said respective elevation leg; and d. lower body securing means to restrain the lower body against upward movement when the user pushes upward, said securing means comprising a belt means worn about the user's waist and strap means generally inelastically connecting said belt to said base legs or said subsurface; whereby a user can by pushing with his forearms and hands against said arm rest means elevate himself with respect to said subsurface and thereby at least partially decompress his spine.

16. Apparatus as in claim 15 wherein said securing means comprises means to hold the user's upper legs against upward movement.

17. An apparatus for decompressing the spine of a user by supporting at least some of the user's body weight upon the user's shoulder girdle, the apparatus comprising:

inclined support members which are positioned in spaced parallel relationship at shoulder width to each side of the user who is generally in a seated posture, the incline of the support members being relatively higher under the user's shoulders and inclining downwards towards the user's legs;

handles affixed to each inclined support member, for each receiving one of the user's hands;

two armrest means, each positioned upon an inclined support member above its handle, for supporting the user's forearm;

the elevation and angle of each inclined support member at the juncture of its handle and its armrest means being such that a user positioned with both his hands grasping the handles and both his forearms resting on the armrest means supports at least some of his weight upon his shoulder girdle and upper arms to decompress the same.

18. The apparatus according to claim 17 wherein the armrest means upon each inclined support member extends sufficiently far above the handle affixed to that support member so as to support the user's entire forearm including the elbow.

19. The apparatus according to claim 17 wherein the armrest means comprises:

a pad upon each inclined support member;

20. The apparatus according to claim 17 wherein the handles are protruding from each inclined support member.

21. The apparatus according to claim 20 wherein the handles protrude substantially perpendicular to the incline of each inclined support member.

22. A method of decompressing the spine of a human by supporting at least some of the human's body weight upon his shoulder girdle, the method comprising:

positioning two support members spaced parallel at shoulder width on each side of the human who is generally in a seated posture, each support member being inclined so as to be higher under the human's shoulders and so as to incline downwards towards the human's legs;

causing each hand of the human to rest upon a handle, that is affixed to each inclined support member;

causing each forearm of the human to rest upon an armrest positioned upon each inclined support leg above its handle; and supporting at least some of the human's weight upon his shoulder girdle and upper arms by the resting of his forearms and hands upon each inclined support member and its handle to decompress the spine.

* * * * *